United States Patent [19]

Wetterlin

[11] 4,137,914
[45] Feb. 6, 1979

[54] AEROSOL INHALATION DEVICE

[75] Inventor: Kjell I. L. Wetterlin, S Sandby, Sweden

[73] Assignee: Aktiebolaget Draco, Sweden

[21] Appl. No.: 749,326

[22] Filed: Dec. 10, 1976

[30] Foreign Application Priority Data

Dec. 12, 1975 [SE] Sweden .............................. 7514067

[51] Int. Cl.² ............................................ A61M 15/00
[52] U.S. Cl. ................................... 128/203; 128/266; 128/213 R; 128/208
[58] Field of Search ............... 128/203, 205, 206, 207, 128/208, 209, 210, 211, 266, 173 H, 173.3, 184, 173 R, 213 R

[56] References Cited

U.S. PATENT DOCUMENTS

| 1,449,047 | 4/1922  | Johnson      | 128/203   |
|-----------|---------|--------------|-----------|
| 1,614,532 | 2/1921  | Mobley       | 128/203   |
| 2,574,028 | 11/1951 | Fields et al.| 128/203   |
| 2,585,254 | 2/1952  | Kochner      | 239/272   |
| 2,641,253 | 6/1953  | Engelder     | 128/203   |
| 2,672,144 | 11/1951 | Cohen        | 128/265   |
| 2,699,167 | 1/1955  | Raiche       | 128/216   |
| 2,895,651 | 7/1959  | Mahon et al. | 222/399   |
| 2,987,439 | 6/1961  | Wittlinger   | 167/59    |
| 3,081,223 | 3/1963  | Gunning et al.| 167/39   |
| 3,119,561 | 1/1964  | Wilson       | 239/309   |
| 3,127,058 | 3/1964  | Johnston     | 128/203   |
| 3,187,748 | 6/1965  | Mitchell et al.| 128/173 R |
| 3,635,219 | 1/1972  | Altounyan et al.| 128/208 |
| 3,776,227 | 12/1973 | Pitesky      | 128/203   |
| 3,870,046 | 11/1975 | Elliott      | 128/266   |
| 3,926,176 | 12/1975 | Winchell et al.| 128/1.2 |
| 3,998,226 | 12/1976 | Harris       | 128/266   |

FOREIGN PATENT DOCUMENTS

| 132993  | 11/1970 | Denmark. |         |
|---------|---------|----------|---------|
| 2033658 | 7/1970  | Fed. Rep. of Germany. | |
| 7014820 | 11/1969 | Sweden.  |         |
| 349478  | 10/1972 | Sweden.  |         |
| 107990  | 10/1916 | United Kingdom | 128/203 |
| 249854  | 6/1927  | United Kingdom. | |
| 329778  | 5/1930  | United Kingdom. | |
| 830427  | 3/1960  | United Kingdom. | |
| 922310  | 3/1963  | United Kingdom. | |
| 977894  | 12/1964 | United Kingdom. | |
| 1269811 | 4/1972  | United Kingdom. | |

OTHER PUBLICATIONS

Derwent Patent Abstract No. 63133t.
Derwent Patent Abstract No. 64980v.
Derwent Patent Abstract No. 88758v.
Derwent Patent Abstract No. 27633r.

Primary Examiner—Henry J. Recla
Attorney, Agent, or Firm—Brumbaugh, Graves, Donohue & Raymond

[57] ABSTRACT

An aerosol inhalation device is designed to use a capsule having a single dose of medication and a propellant. The device includes a hollow needle which perforates the capsule to release the medication. The capsules used with the device include a single dose of medication and an appropriate quantity of propellant.

4 Claims, 2 Drawing Figures

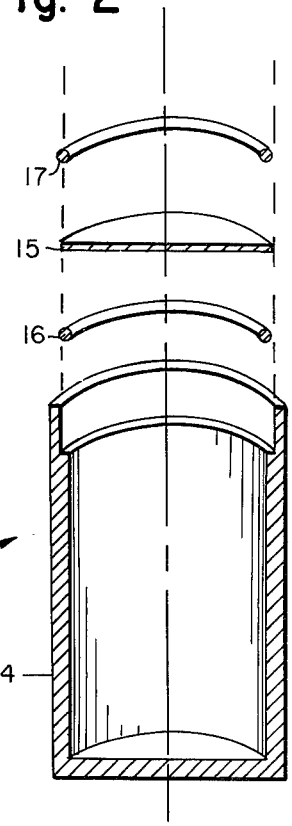
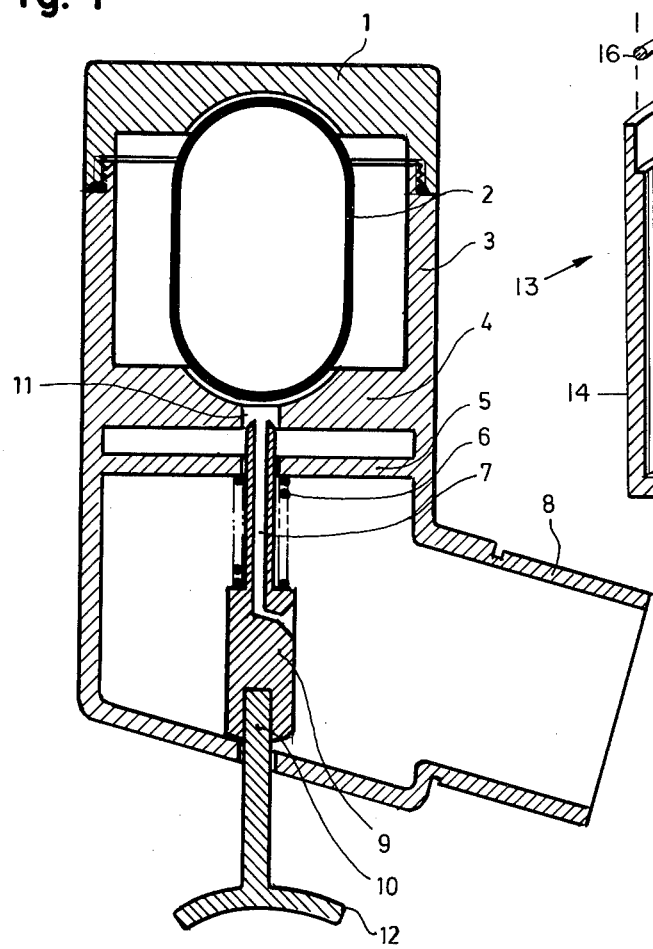

AEROSOL INHALATION DEVICE

BACKGROUND OF THE INVENTION

The present invention relates to aerosol inhalation devices for application of medication to the respiratory tract.

Aerosol inhalation devices are primarily used for local application of medications to the lower parts of the respiratory tract. Such local administration of medication results in rapid response to the medication with a low dosage as compared to systematic administration of the same drug.

Aerosol devices for administration of medication must be designed to have suitable spraying properties, which are reproducible during the useful lifetime of the inhalation device. In order to achieve uniform spraying properties, it is necessary for the propellant pressure of the device to remain constant. The propellant pressure should be also selected to be adequate to produce a fine spray. If spray particles are excessively large, they will be deposited primarily in the oral cavity or upper respiratory tract.

Conventional inhalation devices, such as described in U.S. Pat. Nos. 3,001,524 and 3,012,555 make use of a comparatively large container having both medication and propellant, which is permanently mounted to a dispensing unit. The medication is either dissolved or suspended in the propellant which is typically a chlorofluoroalkane, such as Freon ®. Such fluorocarbon-type propellants have a pressure of 0.3 to 0.5 $\times$ $10^6$ Pascal (3000 to 5000 gm/cm$^2$) at room temperature and have previously been considered to have low toxicity. Fluorocarbon propellants have therefore gained wide use in inhalation devices as well as many other aerosols. Recently, the toxicity of fluorocarbon propellants has been questioned, and recommendations have been made to use substitute propellants in medical inhalation devices (see Toxicology 3 (1975), pp. 321-332). In addition, some scientists have raised questions regarding the possibility that fluorocarbon propellants contribute to the depletion of the atmospheric ozone layer.

Prior inhalation devices have further disadvantages since the permanent mounting of the dispensing apparatus to the medication container results in the disposal of the rather expensive dispensing apparatus when the container is empty. Further, the available pressure in these units is limited by the container to no more than 0.5 $\times$ $10^6$ Pascals (5000 gm/cm$^2$). This is a distinct disadvantage, since higher propellant pressure can produce in a more finely divided aerosol spray, resulting in more rapid propellant evaporation and more uniform medication distribution within the respiratory tract. Another problem with prior aerosol devices is that they are susceptible to excess use by the patient. These devices permit medication to be applied with each breath and contain sufficient medication for approximately 200-400 inhalations. The patient may therefore tend to apply more medication than is appropriate.

While it is evident that it is desirable in an inhalation device to use a non-toxic propellant, such as carbon dioxide, prior art aerosol mechanisms using carbon dioxide as a propellant are not appropriate for use in inhalation devices. Prior art carbon dioxide propelled mechanisms make use of dissolved carbon dioxide to produce spraying pressure. This is unsuitable for an aerosol inhalation device because the propellant pressure decreases as the contents of the container are reduced. Such decrease in propellant pressure reduces the ability of the inhalation device to apply medication to the lower respiratory tract.

It is therefore an object of the present invention to provide an aerosol inhalation device capable of using propellants other than fluorocarbons.

It is a further object of the invention to provide such a device with uniform aerosol properties.

It is a still further object of the invention to provide such a device which does not lend itself to excess use by the patient.

SUMMARY OF THE INVENTION

In accordance with the invention, there is provided an aerosol inhalation device for use with a capsule containing a unit dose of medication. The capsule contains a propellant and includes a penetrable membrane. The inhalation device includes an outlet adapted for insertion in a patient's mouth and containing a spray nozzle. Means are provided for retaining the medication containing capsule. The device also includes a perforating needle with a longitudinal capillary tube communicating with the spray nozzle. The needle and the retaining means are arranged to permit mutual displacement of the needle and the capsule, so that the needle can perforate the capsule and permit the medication to be supplied to the nozzle through the tube.

In a preferred embodiment, the retaining means includes a pair of oppositely facing cup-shaped members. A central opening is provided in one of the cup-shaped members and the needle, which is mounted to the nozzle is displaceable through the opening. Alternately, one of the cup-shaped members may be displaceable to move the capsule onto a fixed needle. The device may include a magazine having a plurality of capsules which is automatically advanced by operation of the inhalation device.

In accordance with a further aspect of the invention, there is provided a medication capsule for use with an aerosol inhalation device. The capsule includes a shell, including a penetrable membrane and having an interior volume of less than 2.0 $cm^3$. The shell contains a propellant and a unit dose of medication, the dose including less than 20 mg of a medically active ingredient.

In a preferred embodiment, the dose has between 0.2 and 2.0 mg of medically active ingredient. The propellant is preferably carbon dioxide and provides an internal pressure in the capsule of 0.3 to $1.0 \times 10^6$ Pascals (3000 to 10000 $gm/cm^2$).

For a better understanding of the present invention, together with other and further embodiments, reference is made to the following description taken in conjunction with the accompanying drawing, and its scope will be pointed out in the appended claims.

BRIEF DESCRIPTION OF THE DRAWING

FIG. 1 is a cross-sectional view of an inhalation device in accordance with the invention.

FIG. 2 in an exploded cross-sectional view of an alternative capsule.

DESCRIPTION OF THE INVENTION

Referring to the FIG. 1, there is shown a capsule 2 which is mounted within a inhalation device between housing members 1 and 4. The housing members are provided with cup-shaped receptacles which are adapted to receive the ends of capsule 2 and firmly retain the capsule in a position for perforation by hollow needle 7. The side wall 3 of housing member 4 is provided with a threaded or clip type connector to retain housing member 1. The inhalation device is provided with an inhalation outlet section 8 which is adapted for insertion into a patient's mouth. Within the outlet 8, there is located a spray nozzle 9 which is connected to hollow needle 7. The spray nozzle 9 and needle 7 are moveably mounted within the device by guide member 5 and equipped with activating member 10 having a finger grip 12 and return spray 6. To activate the inhalation device, a patient displaces finger grip 12 to drive needle 7 through the central opening 11 in cup-shaped member 4 to puncture capsule 2 and therefore release its contents in aerosol form through the center of needle 7 and out the inhalation outlet 8. Needle 7 has an internal passage 0.25 to 1.00 mm in diameter.

It will be evident to those skilled in the art that the same result may be achieved if housing member 1 is moveable and needle 7 is fixed, so that capsule 2 may be forced downwardly by pressure on housing member 1 onto the hollow needle 7 to effectuate puncture of the capsule.

Since capsule 2 rapidly empties after puncture, administering its contents, it is not necessary to provide seals or dosage measuring mechanisms on the inhalation device. Uniformity of pressure and dosage are assured by use of a new capsule on each operation. In oder to coordinate release of the medication with patient's breathing, the needle may be spring loaded and released by the action of a piston or diaphragm under the influence of a patient's inhaling through the outlet. The outlet 8 may be equipped with vents to facilitate patient's breathing during use.

Capsule 2 is designed to contain a single unit dosage of medication and pressurized propellant for administering the single dose. Thus, following activation of the device, the unit capsule 2 must be either manually or automatically replaced by another capsule. Automatic replacement may be achieved by mounting a number of capsules for example 5 or 10 on a belt or rotating magazine. Activation and return of button 12 can be used to activate an automatic mechanical advance of the capsule containing cartridge. Manual advancement of the magazine is also possible. In the simpler embodiment illustrated in FIG. 1, the capsule is manually replaced by unscrewing housing member 1, removing the expended capsule, and inserting a replacement capsule.

The unit dose capsules of the present invention enable the use of a wide variety of propellant gasses or liquids. In addition to commonly used fluorocarbons, non-toxic gasses, such as carbon dioxide, oxygen or nitrogen may be used as propellants. The pressure within the capsule may be selected to be appropriate to the form of medication used, but will preferably be in the range of 0.3 to $1.0 \times 10^6$ Pascals (3000 to 10000 gm/cm$^2$).

The capsule preferably contains a medically active ingredient in either crystalized or liquid form, either suspended or dissolved in a solvent. An active ingredient in the form of a powder may also be used. The amount of active ingredient is less than 20 mg, and preferably between 0.2 and 2.0 mg. The volume of the solvent containing the active substance is preferably between 0.05 and 0.15 cm$^3$. The capsule has a volume of less than 2.0 cm$^3$, and preferably between 0.3 and 1.5 cm$^3$.

The capsule may be made of plastic or metal with a wall thickness suitable to withstand the required internal pressure, but sufficiently thin to permit penetration by the needle in the inhalation device. The capsule may be manufactured in two parts into which the medication and a frozen pellet of carbon dioxide or other propellant are placed prior to joining the parts, which are than either glued or fused together. Alternately, as shown in FIG. 2, a metal capsule 13 may be made in the shape of a cylindrical can 14 with one closed end. A bore extending a short distance along the inner wall of the open end provides a recess for retaining a circular membrane 15. After filling the capsule, a membrane of aluminum foil 0.2 mm thick may be inserted in the bore. Suitable O-rings 16 and 17 are provided on either side of the membrane to provide pressure sealing. The membrane and O-rings are retained by mechanically folding the side walls of the can inward to hold the membrane.

While there has been described what are believed to be the preferred embodiments of the invention, those skilled in the art will recognize that other and further modifications may be made thereto without departing from the spirit of the invention, and it is intended to claim all such embodiments as fall within the true scope of the invention.

I claim:

1. Aerosol inhalation apparatus comprising a capsule having a penetrable membrane and containing a unit dose of medication and a unit quantity of pressurized propellant, a housing having inhalation outlet means adapted for insertion into a patient's mouth, first and second capsule retaining means, mounted in said housing, for retaining said capsule, and a perforating needle slideably mounted in said housing and having one end thereof passing through said first retaining means and an opposite end thereof being located in said outlet means, said needle having at said one end piercing means for piercing said capsule and a spray nozzle at said opposite end thereof in said inhalation outlet and a longitudinal capillary tube connected to said nozzle and extending through said piercing means whereby, said needle and said retaining means are arranged in said housing for mutual displacement between said capsule and said needle to cause said needle to perforate said membrane and cause said propellant to propel said medication through said capillary tube and out said nozzle.

2. Apparatus as specified in claim 1 wherein said first and second capsule retaining means comprise mutually facing cup-shaped members.

3. Apparatus as specified in claim 1 wherein said first retaining means is fixedly mounted to said housing and said needle is displaceably mounted to said housing for movement through an opening on said first retaining means.

4. Apparatus as specified in claim 1 wherein said needle is stationary with respect to said housing and wherein at least a part of said retaining means is moveably mounted with respect to said housing.

* * * * *